United States Patent [19]

Nelson

[11] Patent Number: 5,304,725
[45] Date of Patent: Apr. 19, 1994

[54] ELITE WHITE SPRUCE HYBRIDS AND METHOD OF PRODUCTION

[75] Inventor: Neil D. Nelson, Rhinelander, Wis.

[73] Assignee: Forgene, Inc., Rhinelander, Wis.

[21] Appl. No.: 911,264

[22] Filed: Jul. 7, 1992

Related U.S. Application Data

[63] Continuation of Ser. No. 418,571, Oct. 10, 1989, abandoned.

[51] Int. Cl.[5] .......................... A01H 5/00; A01H 1/02; A01H 1/00; C12N 5/00
[52] U.S. Cl. .................................... 800/200; 800/250; 800/DIG. 49; 435/240.45; 435/240.54; 47/58
[58] Field of Search .................. 435/240.45, 240.54; 800/200, 250, DIG. 49; 47/58.03

[56] References Cited

U.S. PATENT DOCUMENTS 4,417,417 11/1983 Mehra-Palta .......................... 47/58

OTHER PUBLICATIONS

Rumary et al. 1984. Can. J. For. Res. 14:10–16.
Patel et al. 1986. Tree Physiology 1:289–301.
Chalupa, V. 1987. Biologia Plantarum 29(6): 425–429.
Ying, C. 1978. Silvae Genetica 27:226–229.
Mason et al. 1986. Forestry 59:155–171.
Johnsen, O. 1985. Forest Ecol. and Management 11:271–282.
Nienstaedt et al. 1972. Forest Service Research Paper, USDA WO-15.
Nienstaedt, H. and R. M. Jeffers, 1970, "Potential Seed Production from a White Spruce Clonal Seed Orchard," *Tree Planters Notes*, 21(3):15–17.
Nienstaedt, H., 1982, "White Spruce in the Lake States," *Proc. Artificial Regeneration of Conifers of the Upper Great Lakes Region*, Michigan Technological University, Houghton, pp. 142–167.
Stellrecht, J. W., et al., 1974, "Productivity of White Spruce Seed Source in a Minnesota Test Planting," *Minnesota Forestry Research Notes*, No. 251, 4 pages.
Nienstaedt and Riemenschneider, 1985, "Changes in Heritability Estimates with Age and Site in White Spruce, *Picea glauca* (Moench) Voss," *Silvae Genetica*, 34:34–41.
Libby, W. J. and R. M. Rauter, 1984, "Advantages of Clonal Forestry," *Forestry Chronicle*, 60:145–149.
George, E. F. and E. D. Sherrington, 1984, "Plant Propagation by Tissue Culture," *Handbook and Directory of Commercial Laboratories*, Exegetics Limited, Eversley, Basingstoke, Hants., England, 444–447.
Hakman, I.E. and S. von Arnold, 1985, "Plantlet Regeneration Through Somatic Embryogenesis in *Picea abies* (Norway Spruce)," *J. Plant Physiology*, 121:149–158.
Lloyd, G. and B. McCowan, 1980, "Commercially-Feasible Micropropagation of Mountain Laurel, *Kalmia latifolia* by Use of Shoot-tip Culture," *Proc. Intern. Plant Prop. Soc.*, 30:421–427.
Schenk, R. U. and A. C. Hildebrandt, 1972, "Medium and Techniques for Induction and Growth of Monocotyledonous and Dicotyledonous Plant Cell Cultures," *Can. J. Botany*, 50:199–204.
Kleinschmit, J. and J. Schmidt, 1977, "Experiences with *Picea abies* Cuttings Propagation in Germany and Problems connected with large-scale application," *Silvae Genetica*, 26:197–203.
Rauter, R. M. and J. V. Hood, 1981, "Uses for Rooted Cuttings in Tree Improvement Programs," *Proc. in 18th Meet. Can. Tree Improve. Assoc.*, 82–91.
Phillion, B. J., 1983, "Large Scale Production of Black Spruce Cuttings for Progeny Tests," *Internat. Plant Prop. Soc. Comb. Proc.*, 32:619–625.

(List continued on next page.)

*Primary Examiner*—David T. Fox
*Attorney, Agent, or Firm*—Ross & Stevens

[57] ABSTRACT

Elite white spruce hybrid trees, which will grow faster than normal spruce trees, are developed by clonal propagation techniques, including genetic testing, breeding, micropropagation and vegetative propagation.

45 Claims, 2 Drawing Sheets

OTHER PUBLICATIONS

Thompson, D. G., 1984, "Clonal Reforestation; Forests of the Future?" *Seedling Physiology and Reforestation Success*, Martinous Nijoff/Dr. W. Junk, Boston, pp. 1-28.

"Genetically Improved Root Cuttings of Interior Spruce FRDA Project 1.14," 1988, FRDA Research Memo No. 071, Canada BC Economic Development Agreement.

Mason, W. L. and J. C. Keenleyside, 1988, "Propagating Sitka Spruce Under Intermittent Mist and Other Systems," *International Plant Propagators Society Combined Proc.*, 37:294-303.

Pfeifer, A. R., 1988, "Clonal Forestry-A View to the Future," *Irish Forestry*, 45:101-111.

Thorpe, T. A. and S. Biondi, 1984, *Handbook of Plant Cell Culture*, vol. II, Macmillan Publishing Company, New York, pp. 435, 450.

Von Arnold, S. and T. Erikkson, 1985, "Initial Stages in the Course of Adventitious Bud Formation on Embryos of *Picea abies*," *Physiol. Plant*, 64:41-47.

Attree, S. M., et al., 1989, "Plantlet Regeneration from Embryogenic protoplasts of White Spruce (*Picea glauca*)," *Bio/technology*, 7:1060-1062.

ELITE WHITE SPRUCE HYBRIDS AND METHOD OF PRODUCTION

This is a continuation of copending application(s) Ser. No. 07/418,571 filed on Oct. 10, 1989, now abandoned.

FIELD OF THE INVENTION

The present invention is directed to methods of producing plants in general, specifically to methods of producing conifer hybrids, and more specifically to methods of producing elite white spruce hybrids.

DESCRIPTION OF PRIOR ART

White spruce is the third-most planted forest tree species in North America and is near the top in seedling market value. White spruce is a valued landscape and Christmas tree, is widely planted in the Lake States and northeastern United States and throughout Canada for wood production, and is planted throughout much of North America as amenity plantings, i.e., soil conservation, wildlife habitat, windbreaks, shelter belts, privacy screens, border plantings and scenic beautification. Consequently, white spruce seedlings have high intrinsic market value. Current sales of conventional white spruce seedlings in North America are approximately 143 million units per year valued at $36,000,000.00, which indicates the well developed market for this species.

White spruce generally has been sold as seedlings, i.e., trees originated from seeds. Accordingly, conventional genetic tree improvement or breeding programs have centered around the production of improved seed. White spruce, however, has a general reputation as a slow growing tree. Because white spruce seed orchards do not produce appreciable numbers of flowers until they are 9-25 years old (Nienstaedt, H. and R. M. Jeffers, 1970, "Potential Seed Production from a White Spruce Clonal Seed Orchard," *Tree Planters Notes*, 21(3): 15-17), one generation of improvement requires at least nine years. Estimates of genetic gains in height in one improvement cycle (9-25 years range from 9 to 20% (Nienstaedt, H., 1982, "White Spruce in the Lake States," *Proc. Artificial Regeneration of Conifers in the Upper Great Lakes Region*, Michigan Technological University, Houghton, pp. 142-167). Reference is made to Nienstaedt, H. and A. Teich, 1972, "The Genetics of White Spruce," *Forest Service Research Paper*, USDA WO-15, which is incorporated herein by reference, for a general review of the genetics of white spruce.

Dramatic increases in white spruce growth rate would be highly valued for most of the purposes for which it is planted. For example, Christmas tree growers could produce a tree for market in less time, decreasing production costs, accelerating cash flow and capitalizing on the premium paid for spruces in the Christmas tree market. Nurseries could raise trees to landscape size in less time, again reducing production cost and accelerating cash flow. Further, forest products companies could sharply reduce rotation lengths, i.e., the number of years from planting to harvest.

SUMMARY OF THE INVENTION

It is therefore an object of the present invention to develop elite white spruce hybrids which will grow faster than the unimproved trees which currently constitute the market.

It is another object of the present invention to develop rapid cloning methods for conifer trees.

It is another object of the present invention to develop rapid cloning methods for white spruce hybrids to produce elite genotypes of white spruce trees.

It is further an object of the present invention to develop clonal propagation techniques, including cell and tissue culture techniques, for the production of genetically superior white spruce hybrids.

It is still further an object of the present invention to produce a selection and propagation system that integrates conventional genetic testing, breeding, micropropagation and vegetative propagation into a cost effective system for producing high value-added genetic improvement in the white spruce species.

It is another object of the invention to develop elite white spruce hybrids which will grow up to 146% faster than the unimproved material which currently constitutes the market.

These objects, and others are addressed by the present invention, which is designed to develop elite white spruce hybrids. The basic steps for the process include selecting genetically superior white spruce trees for use as female parent trees and male parent trees, crossing the trees selected as parents by pollinating female strobili on trees selected as female parents with pollen from the male strobili from separate trees selected as male parents, recovering high purity hybrid seeds from the trees used as female parent trees, and growing elite white spruce hybrid trees of a size and form suitable for planting in vivo from the seeds.

The approach is based on cloning crosses between tested genetically superior parent trees with the final product being containerized rooted cuttings. Tissue cultures will be used for initial multiplication of the seed resulting from controlled pollinations, i.e., hybridizations, followed by vegetative propagation, i.e., rooting of cuttings, for mass production.

The process for producing elite white spruce hybrids comprises selecting genetically superior parent spruce trees, crossing the male and female parent trees by pollinating the female strobili (flowers) on trees selected as female parents with pollen from the male strobili on separate trees selected as the male parents, recovering high purity hybrid seeds from the female parent trees, germinating the seeds in a growing medium, developing plantlets by vegetative clonal propagation, and growing the plantlets into spruce trees of a size and form suitable for planting. Alternatively, the process for producing elite white spruce hybrids can comprise micropropagating the hybrid seed to develop plantlets by tissue culture propagation techniques.

The invention proceeds according to the following steps:

1) Location of genetically elite parent trees.
2) Controlled crossing and seed production.
3) Tissue culture micropropagation (optional step depending upon the number of seeds produced in Step 2).
4) Development of plantlets.
5) Vegetative clonal propagation, i.e., root cuttings.
6) Test for normal growth and form.
7) Rooted cuttings—mixture of elite, genetically superior clones.
8) Continued testing of elite clones for growth rate.
9) Rooted cuttings—super elite clones.

The present invention is also directed to a process for producing elite fast growing white spruce hybrids, comprising selecting genetically superior parent white spruce trees for use as female parent trees and male parent trees, crossing the trees selected as parents by pollinating female strobili on trees selected as female parents with pollen from the male strobili from separate trees selected as male parents, recovering high purity hybrid seeds from the trees used as female parent trees, micropropagating the hybrid seed to develop plantlets by tissue culture propagating techniques, developing further plantlets by vegetative clonal propagation, and growing the plantlets into spruce trees of a size and form suitable for planting.

Further, the present invention is directed to a process for producing conifer tree (gymnosperm) hybrids, comprising selecting genetically superior parent conifer trees for use as female parent trees and male parent trees, crossing the trees selected as parents by pollinating female strobili on trees selected as female parents with pollen from the male strobili from separate trees selected as male parents, recovering high purity hybrid seeds from the trees used as female parent trees, germinating the seeds in a growing medium, developing plantlets by vegetative clonal propagation, and growing the plantlets into trees of a size and form suitable for planting. Alternatively, the hybrid conifer seed can be micropropagated by tissue culture propagation techniques, followed by developing further plantlets by vegetative clonal propagation, and growing the plantlets into trees of a size and form suitable for planting.

The present invention is also directed to seeds and plants produced by the above described processes.

Further objects, features and advantages of the invention will be apparent from the following detailed description when taken in conjunction with the accompanying drawings.

DETAILED DESCRIPTION OF THE INVENTION

While the present invention is specifically directed to the production of elite white spruce hybrids, it is to be understood that the development protocol is equally applicable to conifers in general.

Figure 1:
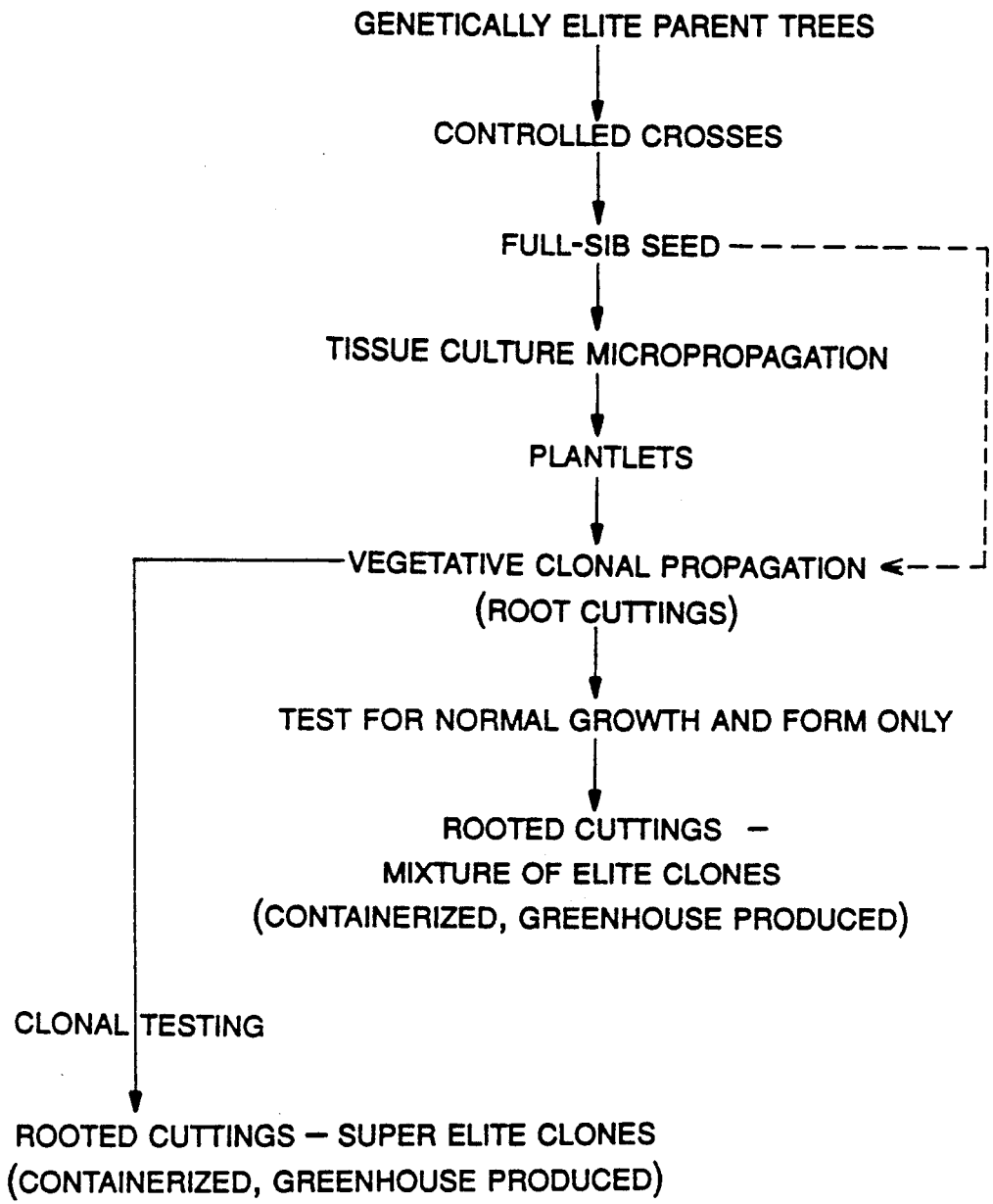
FIG. 1 is a chart indicating the steps for developing clonal elite white spruce hybrids.

Referring now to FIG. 1, the development and production of genetically elite white spruce hybrids according to the present invention is based upon cloning crosses between tested genetically superior parent trees, with the final product being containerized rooted cuttings. The rooted cuttings look exactly like conventional seedlings and are equivalent in size and branching structure to 3-year old seedling transplants of white spruce (2-1 transplants) grown in an outdoor nursery, but are produced in greenhouses on a 6-month cycle.

Genetically Elite Parent Trees

The parent trees used in the controlled crosses were provided by the Wisconsin Department of Natural Resources. The trees were selected from a 19-year old genetic test planting of white spruce located near Lake Tomahawk in northern Wisconsin, one of the most valuable genetics tests of the species in the United States. The genetic superiority of the parent trees and the offspring produced through controlled pollinations between these trees is based on the 19-year genetic test results, other genetic tests and research on white spruce, and the principles of quantitative genetics.

The trees in the genetic test planting were planted in 1969 using 2—2 seedlings grown from open-pollinated seed collected from 61 white spruce trees growing in Michigan, Minnesota and Wisconsin, and 31 white spruce trees located in Renfrew County, Ottawa Valley, Ontario. The Lake States' mother tree sources represent the latitudinal natural range of the species in those three states. The seed from each of the 92 mother trees constituted an open-pollinated family. The families were planted in 1969 near Lake Tomahawk, Wis. in a randomized block design with 10 replications. Each family was represented in each replication by 4-tree line plots. The progeny test trees were measured for total height and diameter at breast height (dbh) in December 1983 at which time 3680 trees remained living in the planting.

Some phenotypic selection was practiced in choosing the 92 mother trees from which seed was collected, e.g., 20 of the Lake States mother trees were considered "Plus Trees" for fast height growth and/or good stem form and/or good general health and vigor and/or desirable crown development and foliage. Although phenotypic selection in the wild and "Plus Tree" designation does not prove genetic superiority, it is a common approach for establishing genetic test plantings, which plantings can be used to prove genetic superiority of families and individuals.

Growth measurements of the material in December 1983, plus other research on white spruce trees, have allowed the identification of the following 19 outstanding parent trees (female parent accession number defines the family):

| Female Parent Accession # | Replication | Tree No. |
|---|---|---|
| 4614 | 10 | 4 |
| 4596 | 10 | 4 |
| 2521 | 10 | 3 |
| 1888 | 10 | 1 |
| 4601 | 10 | 1 |
| 2517 | 10 | 1 |
| 4593 | 9 | 1 |
| 1887 | 9 | 2 |
| 4607 | 8 | 4 |
| 4612 | 8 | 1 |
| 2511 | 5 | 3 |
| 1887 | 5 | 3 |
| 4609 | 5 | 4 |
| 4601 | 5 | 1 |
| 2517 | 3 | 3 |
| 4594 | 3 | 2 |
| 4595 | 3 | 1 |
| 1887 | 1 | 4 |
| 4612 | 1 | 1 |

The 19 parent trees were selected as the fastest-growing trees in the genetic test planting, based on individual tree volume. Tree volumes were calculated as the volume of the bole (inside bark), i.e., main stem, of the tree according to the volume equations in Stellrecht, J. W., et al. (1974) "Productivity of White Spruce Seed Source in a Minnesota Test Planting," *Minnesota Forestry Research Notes*, No. 251, 4 pp., where the volume is a function of diameter of the tree as breast height (outside bark) and total height of the tree. According to these figures, the 19 trees with the best genetic potential for rapid volume growth rate were selected out of the 3,680 in the planting, a selection intensity of 0.005. The actual selection was a combined selection where the trees selected were the best individuals from superior families. The selection was based on an index computed on all trees in the planting based upon their family value combined with their individual phenotypic value. Specifically, the following formula was used:

$$i = b_1 x + b_2 \bar{x}$$

wherein i = combined selection index
x = individual tree value (tree volume)
$\bar{x}$ = mean of family of which individual tree is a member (tree volume)
$b_1, b_2$ = coefficients based on heritabilities
$b_1$ = weight (coefficient) for individual = 0.65
$b_2$ = weight (coefficient) for family = 0.30

Coefficients (weights) were chosen so that the covariance between the selection index and the breeding value of the trees selected is maximum.

Based upon this formula, the 19 trees in the Lake Tomahawk, Wis. genetic test planting having the highest index values were selected as potential parent trees for hybrid production. The 19 trees selected were from three provenances, i.e., original geographic seed sources: Menominee, Wis. area (7 trees, 4 families; 44° 53′ N. latitude); Ottawa Valley area—Renfrew County, Ontario (11 trees, 9 families; 45° 50′–45° 59′ N. latitude); Koochiching County, Minn. area (1 tree, 1 family; 48° 30′ N. latitude). Three of the 19 trees were rejected after a field inspection in March 1988 due to defects including: one trees had several crooks in its stem; two trees had a foliar disease, probably a needle cast disease. Nine of the remaining 16 trees were selected based on individual tree volume and existence of an adequate number of flowers per crossing, and so that there could be at least one cross of each of the following five inter- and intra-provenance hybridization combinations: Menominee x Menominee, Ottawa Valley x Ottawa Valley, Menominee x Ottawa Valley (or reciprocal), Koochiching x Menominee (or reciprocal), and Koochiching x Ottawa Valley (or reciprocal). The identity of the nine trees used in the artificial crosses is given in Table 1 below:

TABLE 1

|  | Male | | | |
|---|---|---|---|---|
|  | 1888-10-1 (Menom.) | 4607-8-4 (Ott.) | 2517-10-1 (Menom.) | 4612-8-1 (Ott.) |
| Female |  |  |  |  |
| 1887-9-2 (Menom.) | X | X | X | X |
| 1887-1-4 (Menom.) | X | X | X | X |
| 4614-10-4 (Ott.) | X | X | X | X |
| 4596-10-4 (Ott.) | X | X | X | X |
| 2511-5-3 (Kooch.) | X | X |  |  |

Inter-provenance crosses (Menom. X Ott., Ott. X Menom., Kooch. X Menom., Kooch. X Ott.) were included to capture the heterosis (hybrid vigor) that can result from crosses between diverse provenances of white spruce (Ying, C. C., 1978, "Height Growth of Inter-provenance Crosses in White Spruce, *Picea glauca* (Moench) Voss. *Silvae Genetica*," 27:226–229), as suggested by Nienstaedt and Riemenschneider (1985), "Changes in Heritability Estimates with Age and Site in White Spruce, *Picea glauca* (Moench) Voss," *Silvae Genetica*, 34:34–41. Thus, the inter-provenance hybrids are likely to have a significantly higher level of genetic improvement in growth rate for the Lake Tomahawk site than the calculated and stated value. The crosses overall were planned to produce hybrids that are broadly adapted and genetically superior in growth rate throughout most of the natural range of white spruce in the U.S. and southeastern Canada, as well as in certain areas south of the white spruce natural range in the U.S.

The narrow-sense heritabilities calculated for the Lake Tomahawk test planting, based on the December 1983 measurements of all trees in the planting, are as follows: total tree height = 0.71, tree diameter (dbh) = 0.53, tree volume = 0.70. The Lake Tomahawk plantation means (December 1983 measurements) were total tree height = 6.16 m, tree dbh = 10.15 cm, tree volume = 242.1 $dm^3 \times 100$. The means for the nine parent trees (December 1983 measurements) were total tree height = 7.79 m, tree dbh = 16.34 cm, tree volume = 665.3 $dm^3 \times 100$.

Using standard quantitative genetics equations for estimating genetic improvement from breeding (see, e.g., Zobel, B. J. and J. T. Talbert, 1984, *Applied Forest Tree Improvement*, John Wiley & Sons, New York, 505 pp.), genetic improvement (genetic gain) of the hybrids over the Lake Tomahawk plantation means was calculated as follows:

genetic gain = narrow-sense heritability × selection differential where selection differential is the difference between the mean of the hybrid parent trees and the plantation mean. The average genetic gain for the 18 hybrids for the Lake Tomahawk site, expressed as a percentage of the Lake Tomahawk plantation mean, is as follows: 19% for height, 33% for diameter, and 124% for volume. The top hybrid is estimated to have a genetic gain (genetic superiority) of 146% on the Lake Tomahawk site.

The crossing and seed production are summarized in Table 2 below:

TABLE 2

| Provenance Hybridization Category* | Female Parent | Male Parent | Number of Filled Seed |
|---|---|---|---|
| MxM | 1887-9-2 | 1888-10-1 | 2,407 |
| MxM | 1887-9-2 | 2517-10-1 | 901 |
| MxM | 1887-1-4 | 1888-10-1 | 3,837 |
| MxM | 1887-1-4 | 2517-10-1 | 1,301 |
| Total MxM |  |  | 8,446 |
| OxO | 4614-10-4 | 4607-8-4 | 406 |
| OxO | 4614-10-4 | 4612-8-1 | 1,284 |
| OxO | 4596-10-4 | 4607-8-4 | 3,100 |
| OxO | 4596-10-4 | 4612-8-1 | 4,012 |
| Total OxO |  |  | 8,802 |
| MxO | 1887-9-2 | 4607-8-4 | 3,074 |
| MxO | 1887-9-2 | 4612-8-1 | 672 |
| MxO | 1887-1-4 | 4607-8-4 | 2,010 |
| MxO | 1887-1-4 | 4612-8-1 | 579 |
| OxM | 4614-10-4 | 1888-10-1 | 751 |
| OxM | 4614-10-4 | 2517-10-1 | 252 |
| OxM | 4596-10-4 | 1888-10-1 | 4,701 |
| OxM | 4596-10-4 | 2517-10-1 | 8,327 |
| Total MxO, OxM |  |  | 20,366 |
| KxM | 2511-5-3 | 1888-10-1 | 1,836 |
| KxO | 2511-5-3 | 4607-8-4 | 1,752 |

*M = Menominee, WI,
O = Ottawa Valley, Ont.,
K = Koochiching County, MN.

Controlled Crosses

A suitable method for conducting controlled crosses on the parent trees is as follows. Isolation bags, i.e., pollination bags, were installed on female parents in time to isolate female strobili from contamination by foreign pollen. The number of bags per tree varies from 2 to 6. Male strobili were collected from male parents on excised male strobili-bearing branches. After being thoroughly washed in tap water, these branches were dried in a forced-air oven at 90° F. The pollen was extracted from the male strobili in a fume hood. The extracted pollen was stored in a dessicator over calcium chloride at room temperature. At pollination time, the pollinations were made using the extracted pollen. The pollination bags were then removed. At this time, all cones were completely closed and had enlarged to more than one-half their mature size. The mature cones were then collected when they had just begun to change from green/purple to a brown color. The scales on the cones on the tree which was most advanced in cone development had begun to open slightly, but no significant loss of seed was evident. The cones were allowed to air dry on a lab bench, after which they were placed in a 90° F. forced-air oven to accelerate drying and opening. The cones were oven-dried in this manner for approximately three days. Seeds were extracted by hand and de-winged immediately after extraction and the winged fragments removed in a seed blower. The seeds were manually counted and obviously underdeveloped seeds were discarded. Following this, the seeds were X-rayed to determine the proportion of filled seed.

A summary of the seed produced is given in Table 3 below. "No. pollinated" is the number of female strobili (flowers) artificially pollinated. "No. cones" is the number of cones that developed to maturity after the female strobili were artifically pollinated. "provenance cross category" defines the inter- or intra-provenance hybridization combination to which the cross belongs. Each filled seed is a separate potential clone.

40° F. in a dessicator over calcium chloride dessicant until use.

Development of Multiple Plantlets

The preferred method for the development of multiple plantlets is to use tissue culture micropropagation for the initial multiplication of the seed resulting from the controlled pollinations, followed by vegetative propagation (rooted cuttings) for mass production. Tissue culture micropropagation is used only for initial multiplication of the plants. However, while it is preferred, this step may be bypassed if there are enough seeds to grow plantlets directly from the seed to the vegetative clonal propagation stage.

Thus, tissue culture is chiefly used to initially multiply scarce genetically improved seeds. Further, clonal propagation techniques have a greater genetic impact then conventional genetic approaches because this method captures genetic values based on both additive and non-additive genetic variance (Zobel, B. and J. Talbert, 1984, supra.) Clonal propagation also has several other advantages over seed propagation of trees as discussed in Libby, W. J. and R. M. Rauter, 1984, "Advantages of Clonal Forestry," *Forestry Chronicle,* 60:145-149.

When fully developed, the controlled cross seeds are removed from the cones and used to develop multiple plantlets of clonal elite white spruce hybrids. Some seeds are also segregated for continued clonal testing for growth rate to identify and produce "super elite" clones. Although spruce trees (Picea sp.) have been subjected to a variety of micropropagation methods, like most other conifers, successful propagation from in vitro cultures has been most commonly obtained via organogenesis involving the formation of adventitious shoots (George, E. F. and P. D. Sherrington, 1984, "Plant Propagation by Tissue Culture," *Handbook and Directory of Commercial Laboratories,* Exegetics Limited, Eversley, Basingstoke, Hants., England). Recent progress has also been achieved with another promising

TABLE 3

Summary of White Spruce Crosses and Seed Produced

| *Prov. Cross Cat. | Female Parent | | Male Parent | No. Pollinated | No. Cones | Total Seed | Filled Seed |
|---|---|---|---|---|---|---|---|
| MxM | 1887-9-2 | x | 1888-10-1 | 41 | 35 | 2546 | 2407 |
| MxO | 1887-9-2 | x | 4607-8-4 | 65 | 59 | 3305 | 3074 |
| MxM | 1887-9-2 | x | 2517-10-1 | 21 | 18 | 1052 | 901 |
| MxO | 1887-9-2 | x | 4612-8-1 | 14 | 14 | 730 | 672 |
| MxM | 1887-1-4 | x | 1888-10-1 | 106 | 101 | 4113 | 3837 |
| MxO | 1887-1-4 | x | 4607-8-4 | 49 | 46 | 2199 | 2010 |
| MxM | 1887-1-4 | x | 2517-10-1 | 45 | 37 | 1614 | 1301 |
| MxO | 1887-1-4 | x | 4612-8-1 | 15 | 15 | 650 | 579 |
| OxM | 4614-10-4 | x | 1888-10-1 | 17 | 13 | 861 | 751 |
| OxO | 4614-10-4 | x | 4607-8-4 | 9 | 9 | 430 | 406 |
| OxM | 4614-10-4 | x | 2517-10-1 | 6 | 5 | 284 | 252 |
| OxO | 4614-10-4 | x | 4612-8-1 | 23 | 22 | 1388 | 1284 |
| OxM | 4596-10-4 | x | 1888-10-1 | 60 | 59 | 4961 | 4701 |
| OxO | 4596-10-4 | x | 4607-8-4 | 83 | 71 | 3457 | 3100 |
| OxM | 4596-10-4 | x | 2517-10-1 | 130 | 115 | 8769 | 8327 |
| OxO | 4596-10-4 | x | 4612-8-1 | 87 | 68 | 4259 | 4012 |
| KxM | 2511-5-3 | x | 1888-10-1 | 42 | 39 | 3076 | 1836 |
| KxO | 2511-5-3 | x | 4607-8-4 | 54 | 52 | 2998 | 1752 |
| | TOTALS | 18 | Crosses | 865 | 778 | 46692 | 41202 |

*M = Menominee, WI,
O = Ottawa Valley, Ont.,
K = Koochiching County, MN.

Overall, 89.9% of the pollinated female strobili matured into cones, and 88.2% of the total seed extracted was filled. The filled seeds were stored at approximately cell and tissue culture approach known as somatic embryogenesis (Hakman, I. and S. von Arnold, 1985, "Plantlet Regeneration through Somatic Embryogenesis in *Picea abies* (Norway Spruce)," *J. Plant Physiol.*, 121:149–158), which can also be used.

Micropropagation

The tissue culture micropropagation stage is the stage in which tissue is excised from a donor plant and nourished on a series of culture media to produce plantlets genetically identical to the donor. There are two approaches to the micropropagation techniques of the present invention: 1) bud induction from embryos and 2) bud induction from seedlings.

The process for inducing buds from embryos of white spruce begins with washing and surface sterilizing the seed. Sterilizing prevents microorganisms, which grow faster than the plant tissue, from contaminating the culture. A preferred method for preparing the tissue is to imbibe and wash the seed in running cold tap water for approximately 16 hours, followed by surface sterilizing the seed with a dilute solution of a commercial bleach, such as 20% Clorox ®, for about 10 minutes. Preferably, the seed is rinsed with sterile distilled water and resterilized with the Clorox ® solution. The seed is rinsed twice again in sterile distilled water. The embryo is then aseptically excised from the seed and placed longitudinally on a bud induction medium consisting of a basal medium with a cytokinin growth regulator and also preferably with thidiazuron (TDZ) added, for a time sufficient to induce formation of adventitious buds on the excised tissue. The cytokinin may be any cytokinin known or discovered to function as a growth factor for gymnosperm tissue. Preferably, the cytokinin will be either BA (benzyladenine=6-benzylaminopurine), kinetin, 2-isopentyladenine (2-iP) or zeatin. A particularly preferred cytokinin is zeatin. TDZ is a diphenyl urea compound with cytokinin-like activity. Agar is the preferred base or substrate for the media. A preferred basal medium is Woody Plant Medium (WPM) (Lloyd, G. and B. McCown, 1980, "Commercially-feasible Micropropagation of Mountain Laurel, *Kalmia latifolia*, by Use of Shoot-tip Culture," *Proc. Intern. Plant Prop. Soc.*, 30:421–427). Alternatively, a half-strength Schenk and Hildebrandt (S & H) medium (Schenk, R. U. and A. C. Hildebrandt, 1972, "Medium and Techniques for Induction and Growth of Monocotyledonous and Dicotyledonous Plant Cell Cultures," *Can. J. Botany* 50:199–204 can be used. Other basal media that are known to be acceptable for conifer tissue culture can also be used. This process takes approximately four weeks.

After this, the explant is immediately transferred to a hormone-free basal medium, the same medium used in the bud induction step without cytokinin and TDZ. The tissue is cultured on this medium for bud development and elongation for a time sufficient to grow visible shoots, usually two to three months. Cultures are then transferred to fresh basal medium monthly. The buds are excised, separated and transferred to fresh basal medium when well distinguished individual shoots are visible. The individual shoots are then allowed to elongate on the basal medium until they are 1.5 cm or greater in length, which requires approximately one to seven months.

When the shoots reach 1.5 cm or greater in length, they are rooted. Roots are induced in vitro or in vivo. Root elongation and development are done in vivo. Root induction in vitro consists of exposure to an auxin in water or in the same type of basal medium in agar used for the cultures prior to rooting, under sterile conditions. Any auxin known or discovered to induce rooting in conifers may be employed. Preferably, the auxin is selected from the group consisting of indole-3-butyric acid, indole-3-acetic acid, 2, 4-dichlorophenoxyacetic acid, and alpha-naphthaleneacetic acid, and mixtures thereof. The basal end of the shoots are exposed to the auxin for 4–14 days. Other compounds in the root induction solution or basal medium can include sucrose, vitamin D, dihydrotachysterol, and rutin. Exposure to the auxin can be in the light or dark at a temperature of 22° to 31° C.

Root induction in vivo (non-sterile) consists of dipping the basal end of the shoot in commercial rooting powders or soaks proven successful with other woody plants, primarily the auxin-based formulations, followed by insertion of the shoot into a non-sterile rooting medium in a growth chamber or greenhouse. Elongation and development of roots are done in a growth chamber or greenhouse in a non-sterile rooting medium. The relative humidity around the shoot is kept high (at or near 100%) during root induction and during the first six to ten weeks of the root elongation and development process, after which relative humidity is gradually lowered to help acclimatize the plantlets. After 10 to 12 weeks of root elongation and development, the plantlets are transferred to soil or other growing medium in a container where root development and acclimatization (gradually lowering relative humidity) continue for another one to three months.

Alternatively, buds can be induced from "1 week or 2 week old" seedlings germinated from aseptically excised embryos on basal media, preferably WPM with agar as the media substrate. Seeds are sterilized and embryos are excised as described previously for bud induction directly on embryos. Embryos are placed on a hormone-free basal medium for one week ("1 week old seedlings") or two weeks ("2 week old seedlings") for germination of seedlings. For the cultures used at 1 week, only seedlings which have hypocotyls over 5 mm in length are used. For the cultures used at 2 weeks, only seedlings which have hypocotyls over 1 cm are used.

The seedlings are divided into two explants 1) the epicotyls and cotyledons, excised just below the swelling at the base of the cotyledons; 2) the apical 5 mm of the hypocotyl. The explants are immediately placed on hormone-supplemented basal media as described previously for bud induction directly on embryos. All general procedures for bud induction, development, and elongation and for rooting are the same as described previously for plantlets derived from buds induced directly on excised embryos.

Vegetative Propagation

Vegetative propagation is the cloning of trees through rooting cuttings of those trees. Vegetative propagation is operational for the commercial production of Norway Spruce planting stock for reforestation in West Germany (Kleinschmit, J. and J. Schmidt, 1977, "Experiences with *Picea abies* Cuttings Propagation in Germany and Problems Connected with Large Scale Application," *Silvae Genetica*, 26:197–203) and for Black Spruce in Canada (Rauter, R. M. and J. V. Hood, 1981, "Uses for Rooted Cuttings in Tree Improvement Programs," *Proc. 18th Meet. Can. Tree Improve. Assoc.*, 82–91; Phillion, B. J., 1983, "Large-Scale Production of Black Spruce Cuttings For Progeny Tests," *Internat. Plant Prop. Soc. Comb. Proc.*, 32:619–625).

The rooted tissue culture shoots, i.e., plantlets, will be repotted as cutting stock plants in the greenhouses. Alternatively and as stated previously, the cutting stock plants are produced directly from seeds in the greenhouse, skipping the tissue culture phase. The cutting stock plants are stimulated to increased production of branches (shoots), preferably by pruning the apical growing point (shoot tip) from the main stem and lateral branches. The cuttings are taken from stock plants and rooted by conventional means in containers to produce the final product, i.e., rooted cuttings of a size and form suitable for planting.

A typical production greenhouse complex usually consists of the following: land, headhouse, greenhouse, shadehouse, refrigerated storage and additional tree processing, grading, and packaging building. The land provides the area for constructing the greenhouse complex. The headhouse is a heated building with water and electricity where growing containers are filled with potting media, fertilizer bulk solutions are mixed, trees are graded and packaged for shipment, and greenhouse materials and supplies are stored.

The greenhouses, where the trees are grown, are typically rigid frame structures with poly-film, glass or fiberglass roof coverings. The greenhouses are heated and have water and electricity.

The shadehouses are generally unheated shelters where seedlings are taken after they have reached full size or near full size in the greenhouses. Some functions of the shadehouse are to allow the seedlings to harden off prior to shipment to the customer, to induce dormancy in the seedlings or to safely store the seedlings over winter. Shadehouses typically have rigid frame structures covered with woven plastic shade cloth or lath to provide approximately 50% shade. Alternatively, shadehouses can be unheated greenhouses with shade cloth over the normal covering.

Refrigerated storage consists of walk-in refrigerators for cold storage of trees after processing, grading and packaging while awaiting shipment to the customers. Refrigerated storage is unnecessary if the trees are transported to planting sites or shipped to customers in the growing containers. Areas in heated buildings in addition to the headhouses are also needed for processing, grading and packaging trees. These are simply open areas in heated buildings that can be used for other purposes during the portion of the year when the trees are not being processed for shipment.

DESCRIPTION OF PREFERRED EMBODIMENTS

Figure 2:
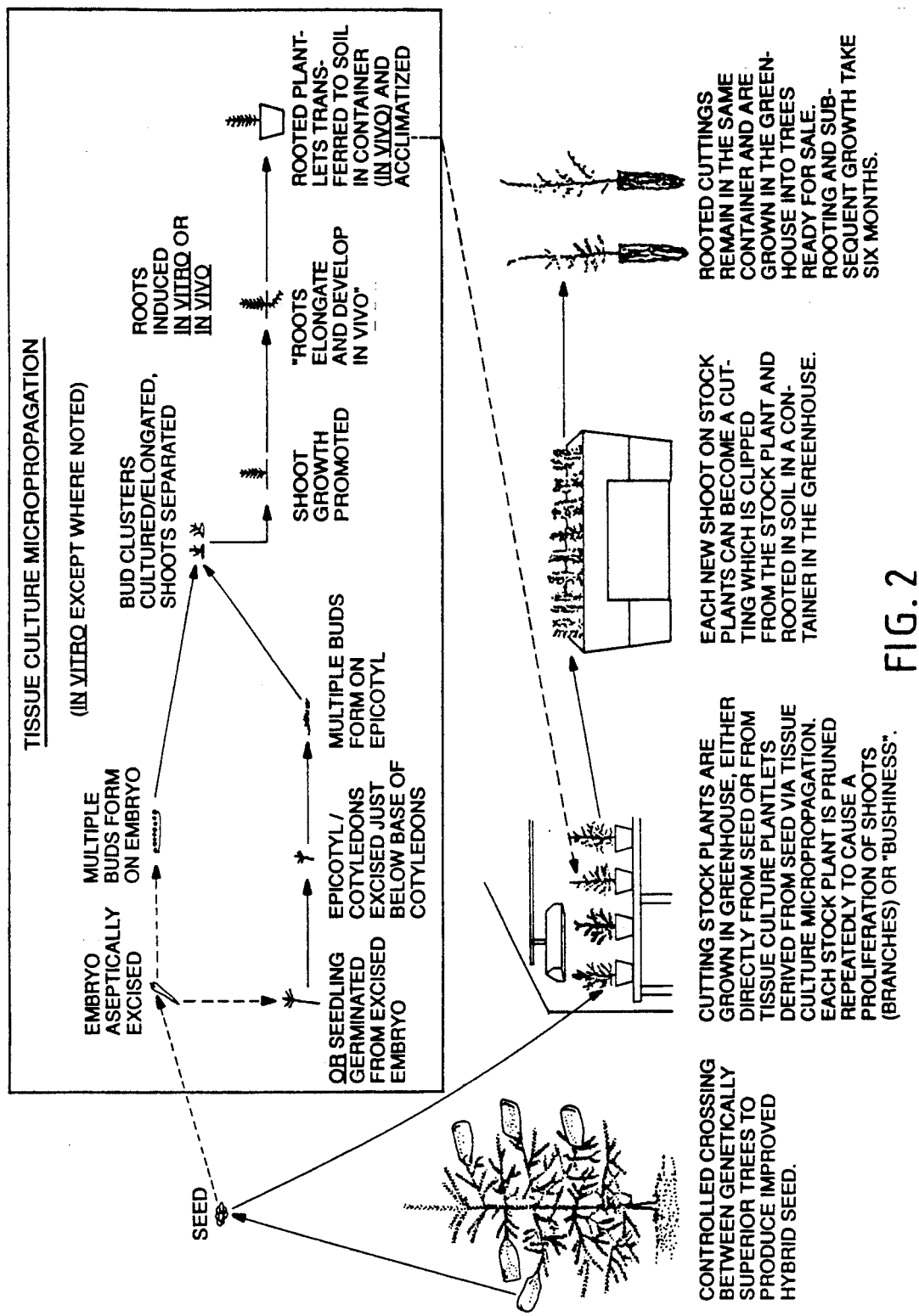
FIG. 2 is a schematic illustrating the steps for producing genetically elite white spruce hybrids.

With reference now to FIG. 2, the following is a detailed discussion of the preferred steps for producing elite white spruce hybrids. The steps are taken and numbered in chronological order.

I. Controlled pollinations are conducted between genetically superior white spruce parent trees, as discussed supra to produce elite full-sib seeds.

II. The seeds are washed and surface sterilized by imbibing and washing the seeds in running cold tap water for approximately 16 hours. Following, the seeds are surface sterilized with a dilute solution of a commercial bleach, such as 20% Clorox ® for about 10 minutes. The seeds are then rinsed in sterile distilled water and resterilized in the bleach solution for another 10 minutes, followed by two more rinsings with sterile distilled water.

Alternatively, the seeds do not need to be washed or sterilized if the tissue culture micropropagation phase is skipped. It is also within the scope of the present invention to provide any surface sterilization procedure known or discovered to be effective for conifer seeds.

III. The embryo is then aseptically excised from the seed.

Alternatively, the embryo need not be excised if the tissue culture micropropagation phase is skipped or if the seed is directly germinated in vitro.

IV. The buds are then induced on the embryo in vitro at 27° C. (for a 24 hour photoperiod under cool white fluorescent lights (20 uE/m$^2$/s PPFD) in small baby food-type jars with translucent plastic caps (5 embryos per jar). The embryos are placed longitudinally on a bud induction medium consisting of WPM and agar supplemented with 50 uM zeatin and 0.01 uM TDZ for a time sufficient to induce formation of adventitious buds on an excised embryo, approximately 4 weeks. The explant is then aseptically transferred to hormone-free WPM in agar and left on this medium until a desired number of the buds have become visible shoots, usually 2 to 3 months, with transfers to fresh WPM monthly.

It is within the scope of the present invention to conduct this step under other culture temperatures, photoperiods, types of lighting, light intensities, sterile containers and covers, basal media, medium substrates, including but not limited to water and Gelrite ®, different numbers of embryos per container, different time periods for tissue on each type of culture, and different types and concentrations of cytokinin and/or compounds with cytokinin-like activity known or discovered to allow bud induction on conifer embryos in vitro.

Different basal media can include one-half strength S&H basal medium in agar, containing cytokinin (1.0 to 100 uM BA if in WPM, 0.1-1.0 uM BA if in half strength S&H, or 10 to 100 uM zeatin). The TDZ concentration can be from 0.0 to 0.1 uM.

Further it is within the scope of the present invention to provide an alternative to Step IV by inducing buds on seedlings germinated from the excised embryo in vitro over a 1 to 2 week period, i.e., "1-week and 2-week seedling," under the same culture environmental conditions as embryo cultures with 5 seedling explants per jar. The embryos are placed longitudinally on WPM in agar in a petri dish for 1 week or 2 weeks for germination of the seedling. At the end of 1 week, only seedlings which have hypocotyls greater than 5 mm in length (or 2 weeks-10 mm) are divided into 2 explants: 1) the epicotyls and cotyledons, excised just below the swelling at the base of the cotyledons; and 2) the apical 5 mm of the hypocotyl. The explants are immediately placed on WPM medium in agar supplemented with 50 uM to 100 uM zeatin and 0.0 to 0.01 uM TDZ ("1-week seedlings") or 10 uM BA and 0.01 uM TDZ ("2-week seedlings") and are kept on the bud induction media for 1 month. The seedling explants are then aseptically transferred to hormone-free WPM in agar and left on this medium until a desired number of buds have become visable shoots, usually 2 to 3 months, with transfer to fresh WPM monthly.

Alternatively, the buds can be induced on seedlings germinated directly from washed and surface sterilized seeds germinated in vitro. The steps are the same as with the previously described process except that the embryo is not excised. In other words, the seed, rather than the embryo, is used in vitro to germinate the seedling.

A further alternative would be to simply delete Step IV if the tissue culture process is skipped. Additionally, Steps II, III and V–VII can be deleted if the tissue culture phase is skipped.

V. The buds are allowed to elongate and develop in vitro under the same culture, light, temperature and container conditions as the bud induction step (Step IV). The individual shoots are aseptically excised, separated and transferred to fresh hormone-free WPM by placing the shoots vertically with the basal end in the medium, and allowing the shoots to elongate on the medium until they are 1.5 cm or greater in length. This step usually requires from 1 to 7 months.

It is within the scope of the present invention to conduct this step under other culture temperatures, photoperiods, types of lighting, light intensity, utilizing other types of containers and covers, basal mediums, medium substrates, and time periods in the culture known or discovered to allow bud elongation of conifer buds in vitro.

VI. The roots are then induced on shoots in vitro by aseptically transferring the shoots to WPM in agar and placing the shoots vertically with the basal end in the medium. The WPM is supplemented with 10 uM indole-3-butyric acid (IBA) (an auxin), vitamin D, and dihydrotachysterol. The shoots are left on this medium in the dark at a temperature of about 22° C. for approximately 14 days.

It is within the scope of the present invention to provide Step VI with different culture conditions, media, hormones, and other conditions which are known or discovered to allow root induction on conifer shoots in vitro. Specifically, the basal medium may be one-half strength S&H. The auxin may include alpha-naphthalene-acetic acid (NAA), indole-3-acetic acid (IAA), 2,4-dichlorophenxyacetic acid (2,4-D) and mixtures thereof, including commercial rooting powders and soaks. The time on the medium can vary from 4 to 14 days or more. The culture temperature can vary from 22°–31° C. and the culture lighting process can be light instead of dark.

A further alternative to Step VI involves root induction in vivo. The in vitro shoots are dipped in commercial rooting powder or soak or IBA, NAA or IAA individually or in mixture or in other auxin or auxins known or discovered to induce roots on conifer shoots in vivo. These shoots are immediately transferred to a non-sterile rooting medium.

It is within the scope of the present invention to provide Step VI with other temperatures, photoperiods, types of growing enclosures, types of growing containers, times allowed for root elongation and development, and times and methods of acclimatization known or discovered to allow root elongation and development and acclimatization of conifer tissue culture plantlets in vivo.

VII. The roots are then allowed to elongate and develop in vivo at a temperature of 22°–31° C. with a 20 hour photoperiod. The tissue culture shoots are transferred to a non-sterile rooting medium in a controlled environment chamber or greenhouse, i.e., a small cell or plug-type container. The containers are covered with clear cellophane or clear plastic wrap or a clear solid plastic top keeping the relative humidity around the plantlets high, i.e., at or near 100% relative humidity, during the first 6 to 10 weeks of root elongation and development, after which relative humidity is gradually lowered over 2 to 4 weeks to closer to normal greenhouse conditions by gradually and partially removing the clear cover over the containers. After 10 to 12 weeks of root elongation, the plantlets are transferred to non-sterile soil or other growing medium in a larger container where root development and acclimatization, i.e., gradually lowering relative humidity, continues for another 1 to 3 months.

It is within the scope of the present invention to provide Step VII with other temperatures, photoperiods, types of growing containers, time periods allowed for root elongation and development, and time periods and methods of acclimatization known or discovered to allow root elongation and development and acclimatization of conifer tissue culture plantlets in vivo.

VIII. The plantlets are then allowed to vegetatively propagate in greenhouses by repotting the micropropagated tissue culture plantlets in 1–2 gallon containers in the greenhouse. At this point, the plantlets become stock plants for cutting production. The stock plants are allowed to grow to a larger size with stimulation to increase production of branches, i.e., shoots, by pruning the apical growing point (shoot tip) from the main stem and lateral branches (shearing) every 2 to 3 months, i.e., between harvests of cuttings. The soft wood cuttings are taken from the stock plants by severing each cutting 4 to 10 cm long, and each containing an intact apical meristem (shoot tip). The cuttings are rooted by conventional means in the containers they will be shipped or transported to the planting site. The cuttings are grown to a final size in the same containers.

Alternatively, the stock plant container may be a 0.25 gallon to 1 gallon or greater than 2 gallon container. The stock plants are allowed to grow by deleting the pruning of the apical growing points of the main stem and branches and/or utilizing a chemical or chemicals to stimulate lateral shoot production and/or lateral shoot growth. Any chemical known or discovered to stimulate formation of increased numbers of lateral shoots and their growth rate in conifers may be used. Shearing the growing stock plants may vary from 1–2 months or greater than 3 months. The cuttings can be taken from stock plants when they are less than 4 cm and more than 10 cm long. The cuttings can also be rooted in a rooting bed or in containers other than the one cutting will be grown in and shipped or transported to the planting site.

Alternatively, the stock plants for cutting production may be established directly from control pollinated hybrid seeds, deleting all tissue culture steps, i.e., Steps II–VII. The seed may be germinated under in vivo non-sterile conditions, grown in containers smaller than 1–2 gallons and then transplanted to the final stock plant growing containers. The rest of the procedure is the same as Step VIII, described above.

EXAMPLES

The following three examples present illustrative but non-limiting embodiments of the present invention. All refer to the bud induction step of the tissue culture micropropagation stage. White spruce seed of Wisconsin origin (Wisconsin DNR Seed Lot No. H-80 collected in Autumn 1980 in northwestern Wisconsin) was used in all three examples. The tissue culture conditions in all examples were as follows: temperature 27° C., 24 hour photoperiod, cool white fluorescent lighting, 20 uE/$m^2$/sec. photosynthetic photon flux density (light intensity), all cultures in small baby food-type jars with screw-cap translucent plastic covers, 5 embryos per jar.

EXAMPLE 1

Bud Induction from Embryos In Vitro

Example 1 was designed to determine the best basal media (Woody Plant Medium (WPM) vs. one-half strength Schenk and Hildebrandt medium (S&H)), the best source of cytokinin (benzyladenine (BA) vs. zeatin), the best concentration of cytokinin, concentration of thidiazuron, and cytokinin-thidiazuron (TDZ) combination for inducing buds on excised embryos from white spruce seeds in vitro.

The seeds were sterilized in 20% Clorox® for 20 minutes (2× for 10 minutes each) and rinsed three times in sterile distilled water. The embryos were aseptically excised from the seed and placed on either WPM or one-half strength S & H basal medium in agar, supplemented with BA, zeatin and/or TDZ, for one month for bud induction. Following the 1-month hormone exposure, the embryos were placed on the same basal medium in agar as they were exposed to in the bud induction step, minus the hormones, for bud development and elongation. Cultures were transferred to fresh basal medium monthly. All bud counts were done after 3 months at the third subculture.

The results of Example 1 are listed in the following table.

The number of buds is expressed as the mean number of buds per surviving embryo (+/− SE).

| TREATMENT | TDZ CONCENTRATION (uM) | | |
|---|---|---|---|
| | 0 | 0.01 | 0.1 |
| WPM -no hormones | 0.1 (0.1) | 4.0 (1.0) | 11.9 (2.4) |
| −0.1 uM BA | 1.5 (0.8) | 3.3 (1.1) | 8.6 (1.5) |
| −1.0 uM BA | 19.8 (2.7) | 9.5 (1.7) | 18.3 (2.4) |
| −10 uM BA | 13.4 (1.7) | 16.6 (3.3) | 13.3 (1.6) |
| −50 uM BA | 14.6 (2.6) | 15.0 (1.5) | 14.8 (1.9) |
| −100 uM BA | 13.7 (2.3) | 12.2 (2.1) | 14.2 (1.7) |
| −10 uM zeatin | 11.0 (3.6) | 10.9 (1.5) | 11.3 (2.1) |
| −50 uM zeatin | 21.5 (4.1) | 31.2 (4.2) | 16.4 (2.9) |
| −100 uM zeatin | 17.0 (2.6) | 19.5 (2.1) | 26.5 (3.0) |
| S&H -no hormones | 0.1 (0.1) | 9.5 (1.3) | 3.1 (0.7) |
| −0.1 uM BA | 8.5 (1.2) | 8.8 (1.6) | 7.4 (1.4) |
| −1.0 uM BA | 8.8 (2.1) | 16.7 (3.1) | 8.3 (1.5) |
| −10 uM BA | 1.7 (1.4) | 1.5 (1.3) | 1.1 (0.6) |
| −50 uM BA | 0.0 (0.0) | 0.0 (0.0) | 0.0 (0.0) |
| −100 uM BA | 0.0 (0.0) | 0.0 (0.0) | 0.0 (0.0) |
| −10 uM zeatin | 16.8 (2.6) | 16.8 (3.0) | 16.2 (3.0) |
| −50 uM zeatin | 37.8 (4.7) | 19.6 (3.6) | 21.6 (3.3) |
| −100 uM zeatin | 35.1 (4.4) | 19.0 (2.5) | 20.4 (2.5) |

EXAMPLE 2

Bud Induction From tissue of Seedlings In Vitro (Seedlings From Excised Embryos Germinated In Vitro Over 1-Week Period)

Example 2 was designed to determine the best basal media (WPM vs. one-half strength S & H), the best source of cytokinin (benzyladenine (BA) vs. zeatin), concentration of cytokinin, concentration of thidiazuron (TDZ), and cytokinin—thidiazuron combination for inducing buds on young white spruce seedling tissue in vitro.

Seeds were sterilized and embryos excised as described in Example 1. Embryos were placed on WPM basal medium in agar in a petri dish for one week for germination of seedlings. At the end of one week, only seedlings which had hypocotyls greater than 5 mm in length were divided into two explants: 1) the epicotyls and cotyledons, excised just below the swelling at the base of the cotyledons; and 2) the apical 5 mm of the hypocotyl. The explants were immediately placed on either WPM or one-half strength S & H medium supplemented with hormones (the bud induction media as described in Example 1) and were kept on the bud induction media for 1 month. Following the 1 month hormone exposure, the seedling explants were placed on the same basal medium in agar as they were exposed to in the bud induction step, minus the hormones, for bud development and elongation. Cultures were transferred to fresh basal medium monthly. All bud counts were done after 3 months, at the third subculture. Most hypocotyl explants did not survive. When they did survive, bud production was low compared to the epicotyl/-cotyledons explants.

The results of Example 2 are listed in the following table. The number of buds is expressed as a mean number of buds per surviving seedling after 3 months (+/− SE).

| TREATMENT | TDZ CONCENTRATION (uM) | | |
|---|---|---|---|
| | 0 | 0.01 | 0.1 |
| WPM -no hormones | 0.0 (0.0) | 1.7 (1.1) | 15.0 (4.1) |
| −0.1 uM BA | 1.3 (0.8) | 5.4 (1.4) | 6.8 (1.4) |
| −1.0 uM BA | 11.3 (2.5) | 8.5 (2.3) | 8.5 (1.4) |
| −10 uM BA | 11.3 (2.6) | 11.7 (2.3) | 13.8 (3.2) |
| −50 uM BA | 18.2 (6.9) | 16.9 (3.2) | 7.6 (2.1) |
| −100 uM BA | 4.0 (1.4) | 8.2 (2.3) | 8.7 (1.8) |
| −10 uM zeatin | 18.4 (3.6) | 17.0 (3.8) | 20.4 (3.6) |
| −50 uM zeatin | 41.1 (8.9) | 26.7 (8.5) | 17.2 (4.7) |
| −100 uM zeatin | 21.8 (4.7) | 34.1 (9.1) | 12.6 (4.0) |
| S&H -no hormones | 0.2 (0.2) | 10.5 (2.8) | 6.0 (1.0) |
| −0.1 uM BA | 4.9 (1.4) | 4.3 (1.0) | 6.8 (1.1) |
| −1.0 uM BA | 17.1 (1.9) | 16.6 (2.7) | 12.1 (2.2) |
| −10 uM BA | 22.4 (3.4) | 26.0 (6.0) | 22.6 (4.9) |
| −50 uM BA | 6.1 (1.7) | 13.9 (4.4) | 12.3 (3.9) |
| −100 uM BA | 3.8 (1.2) | 3.6 (1.2) | 6.8 (1.3) |
| −10 uM zeatin | 22.0 (8.1) | 16.8 (3.6) | 13.8 (3.1) |
| −50 uM zeatin | 20.8 (4.4) | 19.0 (3.4) | 29.4 (5.1) |
| −100 uM zeatin | 26.6 (7.5) | 14.5 (2.8) | 25.7 (3.4) |

EXAMPLE 3

Bud Induction From Tissue of Seedlings In Vitro (Seedlings From Excised Embryo Germinated In Vitro Over a 2-Week Period)

Example 3 was identical to Example 2, except that only seedlings which had hypocotyls greater than 10 mm in length at the end of two weeks on WPM medium were used. As in Example 2, most hypocotyl explants did not survive. When they did survive, bud production was low compared to the epicotyl/cotyledons explants.

The results of Example 3 are listed in the following table.

The number of buds is expressed as a mean number of buds per surviving seedling after 3 months (+/− SE).

| TREATMENT | TDZ CONCENTRATION (uM) | | |
|---|---|---|---|
| | 0 | 0.01 | 0.1 |
| WPM -no hormones | 0.0 (0.0) | 0.0 (0.0) | 0.0 (0.0) |
| −0.1 uM BA | 0.0 (0.0) | 9.0 (4.5) | 1.5 (0.5) |
| −1.0 uM BA | 16.3 (4.8) | 14.9 (4.9) | 11.8 (3.1) |
| −10 uM BA | 16.2 (7.6) | 26.6 (6.5) | 7.6 (3.5) |
| −50 uM BA | 10.6 (1.2) | 22.4 (5.3) | 8.3 (1.1) |
| −100 uM BA | 0.0 (0.0) | 8.1 (1.4) | 5.0 (2.9) |
| S&H -10 uM zeatin | 4.7 (2.3) | 13.4 (4.6) | 8.7 (3.2) |
| −50 uM zeatin | 11.2 (2.9) | 12.0 (4.3) | 18.6 (5.0) |

-continued

| TREATMENT | TDZ CONCENTRATION (uM) | | |
|---|---|---|---|
| | 0 | 0.01 | 0.1 |
| —100 uM zeatin | 9.0 (0.0) | 12.3 (3.8) | 16.6 (3.2) |

It is understood that the invention is not confined to the particular construction and arrangement herein illustrated and described, but embraces such modified forms thereof as comes within the scope of the following claims.

What is claimed is:

1. A process for producing elite white spruce hybrids, comprising:
   (a) selecting from a group consisting of genetically superior white spruce trees a female parent and a male parent, the group of trees being superior in height growth rate, volume growth rate and diameter growth rate;
   (b) crossing the trees selected as parents by pollinating female strobili on a tree selected as the female parent with pollen from male strobili from a tree selected as the male parent, wherein the step of pollinating includes installing isolation bags on the female parent such that the female strobili are isolated from contamination with foreign pollen from non-selected male trees;
   (c) recovering high purity hybrid seeds from the trees used as female parent trees;
   (d) germinating the seeds in a growing medium such that each of the seeds forms a plantlet;
   (e) micropropagating the plantlet of step (d) in a cytokinin-containing basal medium to develop additional plantlets by tissue culture propagating techniques;
   (f) developing additional plantlets from the plantlet of step (d) by vegetative propagation; and
   (g) growing the plantlets into spruce trees of a size and form suitable for planting in vivo.

2. The process of claim 1 wherein the plantlet of step (d) is micropropagated from in vitro tissue cultures via organogenesis involving the formulation of adventitious shoots.

3. The process of claim 1 wherein the micropropagation step includes excising tissue from the plantlet of step (d) and cloning genetically identical plantlets.

4. The process of claim 1 wherein the micropropagating steps comprise:
   (a) washing and surface-sterilizing the seeds;
   (b) aseptically excising the embryos from the seeds;
   (c) including the formation of adventitious buds on the excised embryos by placing the aseptically excised embryo in a bud induction medium including a substrate, a basal medium and cytokinin;
   (d) culturing the buds for a sufficient time to grow visible shoots from the buds;
   (e) separating off the visible shoots;
   (f) allowing the shoots to grow; and
   (g) rooting the shoots.

5. The process of claim 4 wherein the substrate is agar and the basal medium is selected from the group consisting of Woody Plant Medium and half-strength Schenk & Hildebrandt medium.

6. The process of claim 4 wherein the cytokinin is selected from the group consisting of 6-benzylaminopurine, kinetin, 2-isopentyladenine and zeatin, and mixtures thereof.

7. The process of claim 4 wherein the bud induction medium further includes thidiazuron.

8. The process of claim 4 comprising inducing the formation of roots on the shoots in the presence of an auxin.

9. The process of claim 8 wherein the auxin is selected from the group consisting of indole-3-butyric acid, indole-3-acetic acid, 2,4-dichlorophenoxyacetic acid and alpha-naphthaleneacetic acid, and mixtures thereof.

10. The process of claim 4 further comprising rooting the shoots in the presence of vitamin D.

11. The process of claim 4 further comprising rooting the shoots in the presence of dihydrotachysterol.

12. The process of claim 1 further comprising micropropagating the plantlet of step (d) to develop additional plantlets according to the following steps:
   (a) washing and surface-sterilizing the seeds;
   (b) aseptically excising the embryos from the seeds;
   (c) germinating the excised embryos on a hormone-free basal medium to produce seedlings in vitro;
   (d) dividing the seedlings into parts and aseptically excising the seedling parts;
   (e) inducing the formation of adventitious buds on the excised seedling parts in a bud induction medium including a substrate, a basal medium and cytokinin;
   (f) culturing the buds for a sufficient time to grow visible shoots from the buds;
   (g) separating off the visible shoots;
   (h) allowing the shoots to grow; and
   (i) rooting the shoots.

13. The process of claim 12 wherein the substrate is agar and the basal medium is selected from the group consisting of Woody Plant Medium and half-strength Schenk and Hildebrandt medium.

14. The process of claim 12 wherein the cytokinin is selected from the group consisting of 6-benzylaminopurine, kinetin, 2-isopentyladenine and zeatin, and mixtures thereof.

15. The process of claim 12 wherein the bud induction medium further includes thidiazuron.

16. The process of claim 12 comprising inducing the formation of roots on the shoots in the presence of an auxin.

17. The process of claim 16 wherein the auxin is selected from the group consisting of indole-3-butyric acid, indole-3-acetic acid, 2,4-dichlorophenoxyacetic acid and alpha-naphthaleneacetic acid, and mixtures thereof.

18. The process of claim 12 further comprising rooting the shoots in the presence of vitamin D.

19. The process of claim 12 further comprising rooting the shoots in the presence of dihydrotachysterol.

20. The process of claim 1 further comprising micropropagating the plantlet of step (d) to develop additional plantlets according to the following steps:
   (a) washing and surface-sterilizing the seeds;
   (b) germinating the seeds on a hormone-free basal medium to produce seedlings in vitro;
   (c) dividing the seedlings into parts and aseptically excising the seedling parts;
   (d) inducing the formation of adventitious buds on the excised seedling parts in a bud induction medium including a substrate, a basal medium and cytokinin;
   (e) culturing the buds for a sufficient time to grow visible shoots from the buds;
   (f) separating off the visible shoots;

(g) allowing the shoots to grow; and (h) rooting the shoots.

21. The process of claim 20 wherein the substrate is agar and the basal medium is selected from the group consisting of Woody Plant Medium and half-strength Schenk and Hildebrandt medium.

22. The process of claim 20 where the cytokinin is selected from the group consisting of 6-benzylaminopurine, kinetin, 2-isopentyladenine and zeatin, and mixtures thereof.

23. The process of claim 20 wherein the bud induction medium further includes thidiazuron.

24. The process of claim 20 comprising inducing the formation of roots on the shoots in the presence of an auxin.

25. The process of claim 24 wherein the auxin is selected from the group consisting of indole-3-butyric acid, indole-3-acetic acid, 2,4-dichlorophenoxyacetic acid and alpha-naphthaleneacetic acid, and mixtures thereof.

26. The process of claim 20 further comprising rooting the shoots in the presence of vitamin D.

27. The process of claim 20 further comprising rooting the shoots in the presence of dihydrotachysterol.

28. Hybrid seeds produced by the process of claim 1 wherein the seeds are selected from the following female parent and male parent cross 4596-10-4×4612-8-1.

29. White spruce hybrids produced by the process of claim 1 wherein the trees are produced from hybrid seeds from the following female parent and male parent cross 4596-10-4×4612-8-1.

30. A process for producing elite white spruce hybrids, comprising:
(a) selecting from a group consisting of genetically superior white spruce trees a female parent and a male parent, the group of trees being superior in height growth rate, volume growth rate and diameter growth rate;
(b) crossing the trees selected as parents by pollinating female strobili on a tree selected as the female parent with pollen from male strobili from a tree selected as the male parent, wherein the step of pollinating includes installing isolation bags on the female parent such that the female strobili are isolated from contamination with foreign pollen from non-selected male trees;
(c) recovering high purity hybrid seeds from the trees used as female parent trees;
(d) germinating the seeds in a growing medium such that each of the seeds forms a plantlet;
(e) micropropagating the plantlet of step (d) in a cytokinin-containing basal medium to develop additional plantlets by tissue culture propagating techniques;
(f) developing additional plantlets from the plantlet of step (e) by vegetative propagation; and
(g) growing the plantlets of steps (e) and (f) into spruce trees of a size and form suitable for planting in vivo.

31. The process of claim 30 wherein the micropropagation step includes excising the tissue from the plantlet of step (e) and cloning genetically identical plantlets.

32. The process of claim 30 wherein the micropropagation step (e) comprises:
(a) washing and surface-sterilizing the seeds;
(b) aseptically excising the embryos from the seeds;
(c) inducing the formation of adventitious buds on the excised embryos in a bud induction medium including a substrate, a basal medium and cytokinin;
(d) culturing the buds for a sufficient time to grow visible shoots from the buds;
(e) separating off the visible shoots;
(f) allowing the shoots to grow; and
(g) rooting the shoots.

33. The process of claim 32 wherein the substrate is agar and the basal medium is selected from the group consisting of Woody Plant Medium and half-strength Schenk & Hildebrandt medium.

34. The process of claim 32 where the cytokinin is selected from the group consisting of 6-benzylaminopurine, kinetin, 2-isopentyladenine and zeatin, and mixtures thereof.

35. The process of claim 32 wherein the basal medium further includes thidiazuron.

36. The process of claim 32 comprising inducing the formation of roots on the shoots in the presence of an auxin.

37. The process of claim 36 wherein the auxin is selected from the group consisting of indole-3-butyric acid, indole-3-acetic acid, 2,4-dichlorophenoxyacetic acid and alpha-naphthaleneacetic acid, and mixtures thereof.

38. The process of claim 33 further comprising rooting the shoots in the presence of vitamin D.

39. The process of claim 33 further comprising rooting the shoots in the presence of dihydrotachysterol.

40. Hybrid seeds produced by the process of claim 30 wherein the seeds are selected from the following female parent and male parent cross 4596-10-4×4612-8-1.

41. White spruce hybrids produced by the process of claim 30 wherein the trees are produced from hybrid seeds from the following female parent and male parent cross 4596-10-4×4612-8-1.

42. Hybrid seeds produced by the process of claim 1 wherein the seeds are selected from the following female parent and male parent cross 4614-10-4×1888-10-1.

43. White spruce hybrids produced by the process of claim 1 wherein the trees are produced from hybrid seeds from the following female parent and male parent cross 4614-10-4×1888-10-1.

44. Hybrid seeds produced by the process of claim 30 wherein the seeds are selected from the following female parent and male parent cross 4614-10-4×1888-10-1.

45. White spruce hybrids produced by the process of claim 30 wherein the trees are produced from hybrid seeds from the following female parent and male parent cross 4614-10-4×1888-10-1.

* * * * *